United States Patent [19]

Junino et al.

[11] Patent Number: 4,904,276
[45] Date of Patent: Feb. 27, 1990

[54] NITROAMINOPHENOLS, THE PROCESS FOR PREPARATION THEREOF AND THEIR USE IN DYEING KERATINOUS FIBRES, AND NEW INTERMEDIATE NITROAMINOBENZENES AND THEIR USE IN DYEING KERATINOUS FIBRES

[75] Inventors: Alex Junino, Livry-Gargan; Gérard Lang, Saint-Gratien; Alain Genet, Aulnay-sous-Bois, all of France

[73] Assignee: L'Oreal, Paris, France

[21] Appl. No.: 191,075

[22] Filed: Apr. 21, 1988

Related U.S. Application Data

[62] Division of Ser. No. 850,692, Apr. 11, 1986, Pat. No. 4,749,379.

[30] Foreign Application Priority Data

Apr. 16, 1985 [LU] Luxembourg .................. 85853

[51] Int. Cl.$^4$ .................................. A61K 7/13
[52] U.S. Cl. .................................. 8/429; 8/405; 8/407; 8/408; 8/414; 8/416; 549/39
[58] Field of Search ............... 8/429, 414, 416, 407, 8/408, 405; 549/39

[56] References Cited

U.S. PATENT DOCUMENTS

| | | | |
|---|---|---|---|
| 3,794,676 | 2/1974 | Halasz .................. | 8/415 |
| 4,325,704 | 4/1982 | Konrad et al. .......... | 8/409 |
| 4,370,142 | 1/1983 | Bugaut et al. .......... | 8/416 |
| 4,395,262 | 7/1983 | Konrad et al. .......... | 8/423 |
| 4,470,826 | 9/1984 | Bugaut et al. .......... | 8/415 |
| 4,637,821 | 1/1987 | Monnais et al. ........ | 8/408 |
| 4,692,166 | 9/1987 | Junino et al. .......... | 8/410 |
| 4,698,066 | 10/1987 | Rose et al. ............ | 8/416 |
| 4,749,379 | 6/1988 | Junino et al. .......... | 8/408 |
| 4,756,716 | 7/1988 | Rose et al. ............ | 8/414 |

OTHER PUBLICATIONS

Parijs, A. H. "The Replacement of a Nitro Group in 4:5-Dinitrocatechol Methylene Ether and 4:5-Dinitroveratrole by Other Groups", part of a Dissertation, Univ. of Leiden 1928.

Chemical Abstract CA 96(25):217842t Krasso et al. BE890024 Feb. 1982.

Chemical Abstract CA 67(13):62757u Lewis et al. Biochem. Pharmacol. 16(7) 1195-1210 1967.

Primary Examiner—Paul Lieberman
Assistant Examiner—Linda D. Skaling
Attorney, Agent, or Firm—Cushman, Darby & Cushman

[57] ABSTRACT

New nitroaminophenols, the process for preparation thereof and their use in dyeing keratinous fibres, and new intermediate nitroaminobenzenes and their use in dyeing keratinous fibres.

The invention relates to a nitroaminophenol of formula:

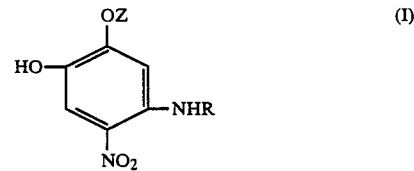

(I)

in which Z denotes -CH$_2$W, W denoting H, C$_1$-C$_6$ alkyl, C$_1$-C$_6$ hydroxyalkyl, C$_2$-C$_6$ polyhydroxyalkyl, (C$_1$-C$_3$), alkoxy(C$_1$-C$_6$)alkyl or (C$_1$-C$_3$)hydroxyalkoxy(C$_1$-C$_6$)-alkyl and R denotes H, (C$_1$-C$_6$)alkyl, C$_1$-C$_6$ hy-droxyalkyl, C$_2$-C$_6$ polyhydroxyalkyl or (C$_1$-C$_3$)-alkoxy(C$_1$-C$_6$)alkyl, and the process for preparation thereof, and the intermediate compound of formula:

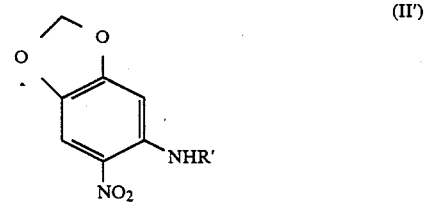

(II')

in which R' denotes C$_1$-C$_6$ hydroxyalkyl, C$^2$-C$_6$ polyhydroxyalkyl or (C$_1$-C$_3$)alkoxy(C$_1$-C$_6$)alkyl and the process for preparation thereof.

The dyes of formulae (I) and (II') can be used in direct dyeing of keratinous fibres, in particular, human hair.

36 Claims, No Drawings

NITROAMINOPHENOLS, THE PROCESS FOR PREPARATION THEREOF AND THEIR USE IN DYEING KERATINOUS FIBRES, AND NEW INTERMEDIATE NITROAMINOBENZENES AND THEIR USE IN DYEING KERATINOUS FIBRES

This is a division of application Ser. No. 850,692, filed Apr. 11, 1986, now U.S. Pat No. 4,749,379.

New nitroaminophenols, the process for preparation thereof and their use in dyeing keratinous fibres, and new intermediate nitroaminobenzenes and their use in dyeing keratinous fibres.

The present invention relates to new nitroaminophenols, the process for preparation thereof, the intermediate nitroaminobenzenes and the use of these two types of compounds as direct dyes in dyeing keratinous fibres, and especially human hair.

In the field of hair dyeing, it is well-known to use so-called oxidation dyes, which perform very well from the technical standpoint in that they lead to shades which have very good covering power and are tenacious. However, these dyes cause the appearance of the phenomenon of boundaries between dyed ends and half-lengths and undyed roots, due to the regrowth of the hair.

For this reason, increasingly frequent use is being made of direct dyes which, by virtue of the variety of possible substituents, enable a broad spectrum of tones to be covered, ranging from yellow to blue passing through orange and red, without it being necessary to lighten the colour of the hair. Added to the fact that these dyes are less resistant to washing, this leads to the disappearance of the phenomenon of boundaries due to regrowth.

Furthermore, these direct dyes, and more precisely the nitrated benzene dyes, which perform best, are also very well tolerated.

However, direct dyes are not free from disadvantages, they are criticized, inter alia, for being insufficiently resistant to washing and light.

During its investigations, the Applicant discovered that it was possible to obtain hair dyes possessing good stability to washing and to adverse weather conditions and good resistance to light by means of a special family of nitroaminophenols.

These compounds enable, in particular, yellow or yellow-orange shades to be provided in hair dyeing formulations, and the hair to be endowed with colours having warm glints.

Furthermore, in addition to their dyeing qualities, these dyes possess the property of being very harmless.

The subject of the present invention is consequently new nitroaminophenols of formula:

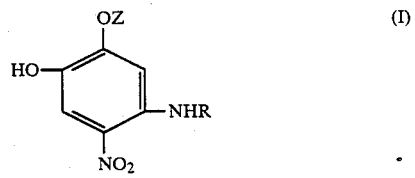

in which:

Z denotes a group —CH$_2$W, W denoting a hydrogen atom or a C$_1$–C$_6$ and preferably C$_1$–C$_4$ alkyl, C$_1$–C$_6$ hydroxyalkyl, C$_2$–C$_6$ polyhydroxyalkyl, (C$_1$–C$_3$)alkoxy(C$_1$–C$_6$)alkyl or (C$_1$–C$_3$)hydroxyalkoxy(C$_1$–C$_6$)-alkyl radical, and R denotes a hydrogen atom or a C$_1$–C$_6$ alkyl, C$_1$–C$_6$ hydroxyalkyl, C$_2$–C$_6$ polyhydroxyalkyl or (C$_1$–C$_3$)-alkoxy(C$_1$–C$_6$)alkyl radical.

By way of preferred radicals Z, methyl, ethyl, n-propyl, β-hydroxyethyl, β, γ-dihydroxypropyl, γ-hydroxypropyl, β-methoxyethyl, β-ethoxyethyl and β-hydroxyethoxyethyl radicals may be mentioned.

By way of preferred radicals R, hydrogen and methyl, ethyl, n-propyl, n-butyl, β-hydroxyethyl, γ-hydroxypropyl, β, γ-dihydroxypropyl, β-methoxyethyl and β-ethoxyethyl radicals may be mentioned.

Among the compounds of formula (I), the following preferred compounds may be mentioned:
2-methoxy-4-methylamino-5-nitrophenol
2-methoxy-4-n-butylamino-5-nitrophenol
2-methoxy-4-(γ-hydroxypropyl)amino-5-nitrophenol
2-(β-hydroxyethoxy)-4-methylamino-5-nitrophenol
2-(β,γ-dihydroxypropoxy-4-n-butylamino-5-nitrophenol
2-methoxy-4-amino-5-nitrophenol
2-ethoxy-4-(β-hydroxyethyl)amino-5-nitrophenol.

The process for preparing the compounds of formula (I), which constitutes another subject of the invention, can be summarized by the reaction scheme below:

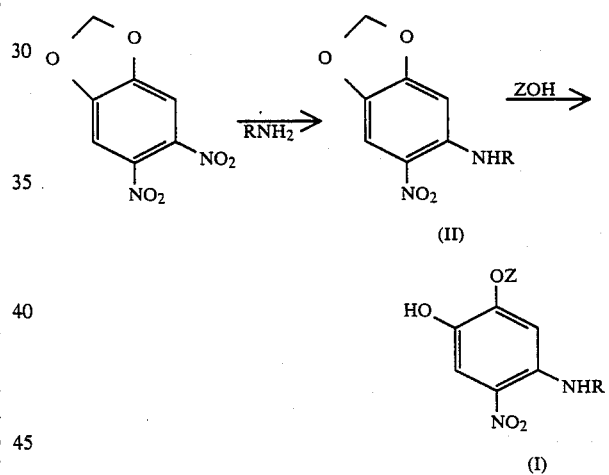

Z and R having the meanings stated above.

The compounds of formula (II) in which R denotes a hydrogen atom or a C$_1$–C$_6$ alkyl radical are known from A. H. PARIJS, Rec. Trav. Chim, 49, pages 45–56 (1930); they are obtained by heating 4,5-methylenedioxy-1,2-dinitrobenzene in an alcoholic solution of ammonia or of a (C$_1$–C$_6$)alkylamine.

The compounds of formula (II) for which R denotes hydroxyalkyl, polyhydroxyalkyl and alkoxyalkyl are new. They are prepared by the action of the amine RNH$_2$ on 4, 5-methylenedioxy-1.2-dinitrobenzene, optionally in the presence of a solvent and optionally in the presence of triethylamine. The reaction temperature is generally that of reflux of the amine or of the solvent if it is present. The preferred solvents are C$_1$–C$_4$ lower alcohols.

In the case of a compound (II) in which R denotes a hydrogen atom, the preferred preparation process is the selective reduction of one of the NO$_2$ groups, accomplished with iron in refluxing acetic acid according to D. S. WULFMAN and C. F. COOPER, Synthesis, page 924 (1978). Another process can be used for accomplishing the reduction; it consists in using stannous chloride dihydrate as a reducing agent in a non-acidic and non-aqueous medium, applying the method described by F. D. BELLAMY, Tetrahedron Letters, 25, page 839 (1984).

By the action of an alcohol of formula WCH$_2$OH on the compounds of formula (II), in the presence of a strong base such as potassium hydroxide at a temperature of between 40° and 120° C., the compounds (I) are obtained. In place of the alcohol and the strong base, a sodium or potassium alcoholate can be used.

Another subject of the invention consists of the compounds of formula (II'):

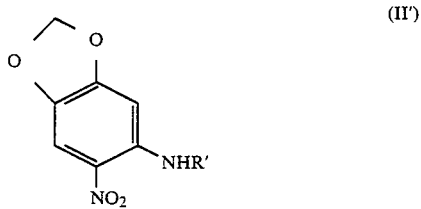

in which:

R' denotes a $C_1$-$C_6$ hydroxyalkyl, $C_2$-$C_6$ polyhydroxyalkyl or ($C_1$-$C_3$)alkoxy ($C_1$-$C_6$)alkyl radical.

Among the preferred compounds of formula (II'), the following may be mentioned:

2-(γ-hydroxypropyl)amino-4,5-methylenedioxy-1-nitrobenzene 2-(β-hydroxyethyl)amino-4,5-methylenedioxy-1-nitrobenzene 2-(β,γ-dihydroxypropyl)amino-4,5-methylenedioxy-1-nitrobenzene 2-(β-methoxyethyl)amino-4,5-methylenedioxy-1-nitrobenzene.

The compounds of formula (I) and the compounds of formula (II) (known compounds and new compounds) can be used as dyes in dyeing compositions for the direct dyeing of keratinous fibres, and especially human hair.

The subject of the present invention is hence also a dyeing composition for keratinous fibres, and especially for human hair, containing at least one compound of formula (I) or (II) in a cosmetically acceptable medium.

The dyeing compositions according to the invention contain the compounds of formula (I) or (II) in proportions of between 0.001 and 5% by weight, and preferably between 0.01 and 3% by weight, relative to the total weight of the dyeing composition.

They can contain anionic, cationic, nonionic or amphoteric surfactants or mixtures thereof. These surfactant products are present in the compositions of the invention in proportions of between 0.5 and 55% by weight, and preferably between 4 and 40% by weight, relative to the total weight of the composition.

The cosmetic vehicle generally consists of water, but organic solvents can also be added to the compositions to solubilize compounds which would not be sufficiently soluble in water. Among these solvents, there may be mentioned lower alcohols such as ethanol and isopropanol, polyols such as glycerol, and glycols or glycol ethers such as 2-butoxyethanol, ethylene glycol, ethylene glycol monoethyl ether, propylene glycol, diethylene glycol monoethyl ether and monomethyl ether, as well as similar products and mixtures thereof. These solvents are preferably present in proportions ranging from 1 to 75% by weight, and especially from 5 to 50% by weight, relative to the total weight of the composition.

The compositions can preferably be thickened with compounds chosen from sodium alginate, gum arabic, xanthan gum, cellulose derivatives such as methylcellulose, hydroxyethylcellulose, hydroxypropylmethylcellulose and carboxymethylcellulose, and various polymers having the function of a thickener such as, more especially, acrylic acid derivatives. It is also possible to use inorganic thickening agents such as bentonite. These thickening agents are preferably present in proportions of between 0.1 and 10% by weight, and especially between 0.5 and 3% by weight, relative to the total weight of the composition.

The compounds according to the invention can also contain various adjuvants customarily used in hair dyeing compositions, and especially penetrants, sequestering agents, film-forming agents, buffers and perfumes.

These compositions can take various forms such as liquid, cream or gel form, or any other form suitable for carrying out dyeing of hair. They can, in addition, be packaged in aerosol cans in the presence of a propellant.

The pH of these dyeing compositions can be between 3 and 11.5, preferably between 5 and 11.5. This is adjusted to the desired value by means of an alcalinizing agent such as ammonia solution, sodium carbonate, potassium carbonate or ammonium carbonate, sodium hydroxide or potassium hydroxide, alcanolamines such as mono-, di- or triethanolamine, or alkylamines such as ethylamine or triethylamine, or by means of an acidifying agent such as phosphoric, hydrochloric, tartaric, acetic, lactic or citric acid.

The dyeing compositions according to the invention can contain, in addition to the compounds according to the invention, other direct dyes such as azo dyes, for example 4-amino-2'-methyl-4'-[bis(hydroxyethyl)amino]azobenzene, or anthraquinone dyes, for example 1,4,5,8-tetraaminoanthraquinone, and nitro dyes of the benzene series other than the compounds of formula (I) or (II), and more especially the following compounds:

3-nitro-4-amino-6-chloro-N-(β-aminoethyl)aniline
3-nitro-4-methylamino-N-(β-hydroxyethyl)aniline
3-nitro-4-amino-N-β-hydroxyethyl)aniline
[3-nitro-4-(β-hydroxyethyl)aminophenoxy]ethanol
3-nitro-4-(β-aminoethyl)amino-N-bis(β-hydroxyethyl)-aniline
3-nitro-4-(β-hydroxyethyl)amino-6-chloroaniline
3-nitro-4-amino-6-methyl-N-(β-hydroxyethyl)aniline
N,N'-bis(β-hydroxyethyl)-4-nitro-ortho-phenylenediamine
2-nitro-N-(β-aminoethyl)aniline
2-methyl-6-nitroaniline
3-nitro-4-aminophenol
3-nitro-4-(β-hydroxyethyl)aminophenol
3-nitro-4-amino-6-methylphenol
3-amino-4-nitrophenol
2-amino-3-nitrophenol
3-nitro-6-(β-hydroxyethyl)aminoanisole
3-(β,γ-dihydroxypropyl)amino-4-nitroanisole
3-methylamino-4-nitrophenoxy)ethanol
3-methylamino-4-nitrophenyl β, γ-dihydroxypropyl ether
N,N'-bis(β-hydroxyethyl)nitro-para-phenylenediamine
3-nitro-4-methylamino-N,N-bis(β-hydroxyethyl)aniline
3-nitro-4-(β-hydroxyethyl)amino-N,N-bis(β-hydroxyethyl)aniline 3-nitro-4-(β-hydroxyethyl)aminoaniline
3-nitro-4-(γ-hydroxypropyl)amino-N,N-bis(β-hydroxyethyl)aniline.

The concentrations of these direct dyes, other than the dyes of formulae (I) and (II), can be between 0.001 and 5% by weight relative to the total weight of the composition.

The present invention also relates to a process for dyeing keratinous fibres, and more especially human hair, by direct dyeing, which consists in applying on the fibres a composition as defined above, leaving the latter in place for 5 to 40 minutes, then rinsing the fibres, optionally washing them, rinsing them again and drying them.

The compositions according to the invention can also be employed in the form of hair setting lotions designed, at one and the same time, to endow the hair with a light colouring and to improve the shape-retention of the set. In this case, they take the form of aqueous, alcoholic or hydroalcoholic solutions containing at least one cosmetic resin, and they are applied on damp hair which has been washed and rinsed beforehand and which is optionally coiled and then dried. The subject of the present invention is consequently a process for dyeing keratinous fibres, and especially human hair, which consists in applying a composition according to the invention on the washed and rinsed fibres, then in optionally coiling the fibres and in drying them.

The cosmetic resins used in the setting lotions can be, in particular, polyvinylpyrrolidone or crotonic acid-vinyl acetate, vinylpyrrolidone-vinyl acetate, maleic anhydride-butyl vinyl ether or maleic anhydridemethyl vinyl ether copolymers, as well as any other cationic, anionic, nonionic or amphoteric polymer customarily used in this type of composition. These cosmetic resins participate in the compositions according to the invention in the proportion of 0.5 to 3% by weight, and preferably 1 to 2% by weight, based on the total weight of the composition.

The present invention will be better illustrated by the following non-limitative examples:

EXAMPLE 1

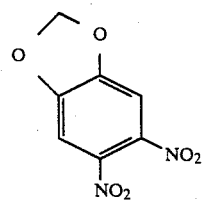

Preparation of 4,5-methylenedioxy-1,2-dinitrobenzene according to D. S. WULFMAN and C. F. COOPER, Synthesis, pages 924–925 (1978)

0.103 mol (17.2 g) of 4,5-methylenedioxy-1-nitrobenzene is added in small portions in the course of 15 minutes to a mixture, cooled to −5° C., consisting of 125 ml of nitric acid (d=1.50) and 125 ml of nitric acid (d=1.40), the temperature being maintained at between 0° and 5° C. 1 hour after the addition is complete, the reaction mixture is poured onto 1 kg of ice. The expected product precipitates. After being dried hot in the presence of phosphorus pentoxide, it melts at 99° C. (literature 98°–100° C.). It can optionally be recrystallized from 96° strength ethanol.

Analysis of the product contained gives the following results:

| Analysis | Calculated for $C_7H_4N_2O_6$ | Found |
| --- | --- | --- |
| C % | 39.63 | 39.81 |
| H % | 1.90 | 1.93 |
| N % | 13.21 | 13.20 |
| O % | 45.26 | 45.15 |

EXAMPLE 2

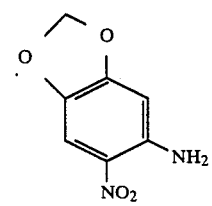

Preparation of 2-amino-4,5-methylenedioxy-1-nitrobenzene 0.25 mol (56.4 g) of stannous chloride containing two molecules of water and 0.05 mol of 4,5-methylenedioxy-1,2-dinitrobenzene are added to 100 ml of ethyl acetate. The mixture is brought for 10 minutes to the refluxing temperature of ethyl acetate.

After evaporation of the ethyl acetate under reduced pressure, an oily residue is obtained which is taken up with 150 ml of water. The expected product precipitates. After being washed with water and dried, it is recrystallized from ethyl acetate. It melts at 198° C. (literature 196°–198° C.).

Analysis of the product contained gives the following results:

| Analysis | Calculated for $C_7H_6N_2O_4$ | Found |
| --- | --- | --- |
| C % | 46.16 | 45.91 |
| H % | 3.32 | 3.33 |
| N % | 15.38 | 15.26 |
| O % | 35.14 | 34.98 |

EXAMPLE 3

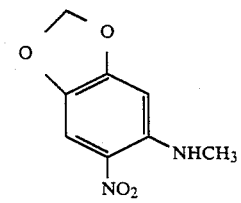

Preparation of 2-methylamino-4,5-methylenedioxy-1-nitrobenzene 0.05 mol (10.6 g) of 4,5-methylenedioxy-1,2-dinitrobenzene is added to 40 ml of a 33% strength solution of methylamine in absolute ethanol to which 20 ml of 96° strength ethanol have been added. The reaction edium is heated under reflux for 30 minutes. After dilution with 150 ml of ice-cold water, the expected product precipitates. After being drained and washed with water, it is recrystallized from a mixture of ethanol and acetone. It melts at 170° C. (literature 171° C.).

Analysis of the product obtained gives the following results:

| Analysis | Calculated for $C_8H_8N_2O_4$ | Found |
|---|---|---|
| C % | 48.98 | 49.00 |
| H % | 4.11 | 4.14 |
| N % | 14.28 | 14.40 |
| O % | 32.63 | 32.40 |

EXAMPLE 4

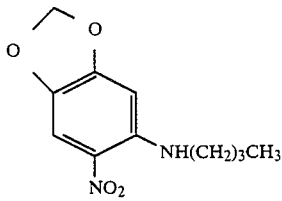

Preparation of 2-n-butylamino-4,5-methylenedioxy-1-nitrobenzene 0.05 mol (10.6 g) of 4,5-methylenedioxy-1,2-dinitrobenzene is added to 40 ml n-butylamine. The reaction is exothermic. The boiling point of butylamine is reached. As soon as the exothermic effect has finished, 200 g of ice are added to the reaction medium. After neutralization of the excess butylamine with concentrated hydrochloric acid, the expected product crystallizes. After recrystallization from 96° strength ethanol or from ethyl acetate, it melts at 137° C. (literature 137° C.).

Analysis of the product obtained gives the following results:

| Analysis | Calculated for $C_{11}H_{14}N_2O_4$ | Found |
|---|---|---|
| C % | 55.45 | 55.49 |
| H % | 5.92 | 5.97 |
| N % | 11.76 | 11.58 |
| O % | 26.86 | 26.75 |

EXAMPLE 5

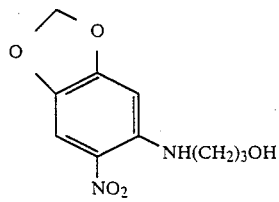

Preparation of 2-(γ,hydroxypropyl)amino-4,5-methylenedioxy-1-nitrobenzene 0.025 mol (5.3 g) of 4,5-methylenedioxy-1,2-dinitrobenzene is added in a single portion to a solution of 0.09 mol (6.9 ml) of propanolamine in 15 ml of 96° strength ethanol. The reaction mixture is heated for 1 hour under reflux. After filtration hot, the expected product crystallizes from the filtrate. After recrystallization from 96° strength ethanol, it melts at 134° C.

Analysis of the product obtained gives the following results:

| Analysis | Calculated for $C_{10}H_{12}N_2O_5$ | Found |
|---|---|---|
| C % | 50.00 | 49.95 |
| H % | 5.04 | 5.06 |
| N % | 11.66 | 11.59 |
| O % | 33.30 | 33.38 |

EXAMPLE 6

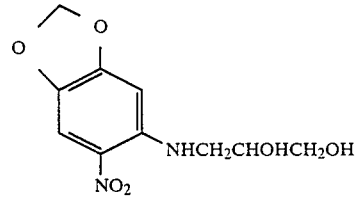

Preparation of 2-(β,γ-dihydroxypropyl)amino-4,5-methylenedioxy-1-nitrobenzene 0.6 mol (56.3g) of 3-amino-1,2-propanediol is added dropwise to a mixture, brought to reflux, prepared by adding 0.3 mol (63.6 g) of 4,5-methylenedioxy-1,2-dinitrobenzene and 46 ml of triethylamine to 90 ml of 96° strength ethanol. The reaction mixture is heated for 3 hours under reflux. After dilution with 600 ml of ice-cold water and neutralization with acetic acid, the expected product is drained. After recrystallization from acetonitrile, it melts at 120°–121° C.

Analysis of the product obtained gives the following results:

| Analysis | Calculated for $C_{10}H_{12}N_2O_6$ | Found |
|---|---|---|
| C % | 46.88 | 46.87 |
| H % | 4.72 | 4.82 |
| N % | 10.93 | 11.13 |
| O % | 37.47 | 37.26 |

EXAMPLE 7

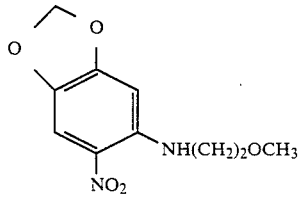

Preparation of 2-(β-methoxyethyl)amino-4,5-methylenedioxy-1,nitrobenzene

A solution of 0.6 mol (45.1 g) of 2-methoxyethylamine in 30 ml of 96° strength ethanol is added dropwise in the course of 20 minutes to a mixture, brought to reflux, consisting of 0.3 mol (63.6 g) of 4,5-methylenedioxy-1,2-dinitrobenzene and 0.33 mol (46 ml) of triethylamine in 90 ml of ethanol. The heating is continued for 10 minutes after the addition is complete.

After the addition of 600 ml of ice-cold water and neutralization with acetic acid, the expected product precipitates. After recrystallization from isopropanol, it melts at 86° C.

Analysis of the product obtained gives the following results:

| Analysis | Calculated for $C_{10}H_{12}N_2O_5$ | Found |
|---|---|---|
| C % | 50.00 | 49.86 |
| H % | 5.04 | 5.07 |
| N % | 11.66 | 11.64 |
| O % | 33.30 | 33.60 |

EXAMPLE 8

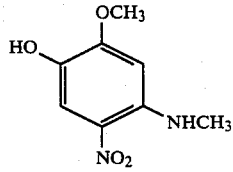

Preparation of 2-methoxy-4-methylamino-5-nitrophenol

A solution of 0.1 mol (19.6 g) of 2-methylamino-4,5-methylenedioxy-1-nitrobenzene, prepared according to Example 3, in 80 ml of a 30% strength solution of sodium methylate in methanol is brought for 15 minutes to the refluxing temperature of the methanol. The reaction medium is diluted with 500 ml of water. After the filtrate has been neutralized with acetic acid, the expected product precipitates.

After recrystallization from methanol, the product obtained melts at 202° C.

Analysis of the product obtained gives the following results:

| Analysis | Calculated for $C_8H_{10}N_2O_4$ | Found |
|---|---|---|
| C % | 48.48 | 48.52 |
| H % | 5.09 | 5.06 |
| N % | 14.14 | 14.32 |
| O % | 32.29 | 32.38 |

EXAMPLE 9

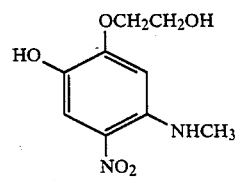

Preparation of 2-(β-hydroxyethoxy)-4-methylamino-5-nitrophenol 0.06 mol (3.9 g) of 85% pure potassium hydroxide pellets is dissolved in 60 ml of ethylene glycol on a boiling water bath. 0.03 mol (5.9 g) of 2-methylamino-4,5-methylenedioxy-1-nitrobenzene, prepared according to Example 3, is added with stirring in the course of 5 minutes.

After 15 minutes' heating, the reaction medium is cooled and diluted with 200 g of ice-cold water. On neutralization with acetic acid, the expected product precipitates.

It is recrystallized from ethylene glycol monomethyl ether. It melts at 217°–219° C.

Analysis of the product obtained gives the following results:

| Analysis | Calculated for $C_9H_{12}N_2O_5$ | Found |
|---|---|---|
| C % | 47.37 | 47.31 |
| H % | 5.30 | 5.32 |
| N % | 12.28 | 12.31 |
| O % | 35.06 | 35.09 |

EXAMPLE 10

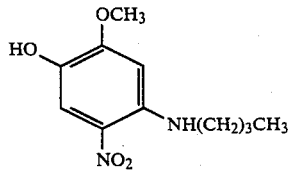

Preparation of 2-methoxy-4-n-butylamin-5-nitrophenol

A solution of 0.03 mol (6.9 g) of 2-n-butylamino-4,5-methylenedioxy-1-nitrobenzene, prepared according to Example 4, in 45 ml of a 30% strength solution of sodium methylate in methanol is brought for 15 minutes to the refluxing temperature of the methanol.

The reaction medium is diluted with 150 ml of water.

After neutralization, the expected product crystallizes.

It is recrystallized from 96° strength ethanol. It melts at 127° C.

Analysis of the product obtained gives the following results:

| Analysis | Calculated for $C_{11}H_{16}N_2O_4$ | Found |
|---|---|---|
| C % | 54.99 | 54.88 |
| H % | 6.71 | 6.73 |
| N % | 11.66 | 11.63 |
| O % | 26.64 | 26.90 |

EXAMPLE 11

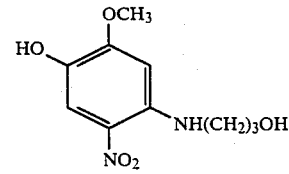

Preparation of 2-methoxy-4-(γ-hydroxypropyl)amino-5-nitrophenol

A mixture consisting of 0.013 mol (3.12 g) of 2-(γ-hydroxypropyl)amino-4,5-methylenedioxy-1-nitrobenzene, prepared according to Example 5, and 22 ml of a 30% strength solution of sodium methylate in methanol are brought to the refluxing temperature of the methanol for 10 minutes.

The reaction medium is diluted with 100 ml of ice-cold water.

After neutralization with acetic acid, the expected product crystallizes. It is recrystallized from 96° strength ethanol. It melts at 144° C.

Analysis of the product obtained gives the following results:

| Analysis | Calculated for $C_{10}H_{14}N_2O_5$ | Found |
|---|---|---|
| C % | 49.58 | 49.40 |
| H % | 5.83 | 5.85 |
| N % | 11.57 | 11.53 |
| O % | 33.03 | 33.17 |

EXAMPLE 12

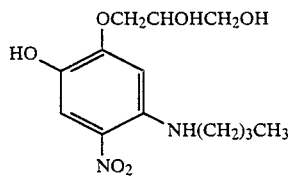

Preparation of 2-(β,γ-dihydroxpropoxy)-4-n-butylamino-5-nitrophenol 0.128 mol (8.5 g) of 85% pure potassium hydroxide pellets is dissolved in 70 ml of double-distilled glycerol on a boiling water bath. 2-n-butylamino-4,5-methylenedioxy-1-nitrobenzene, prepared according to Example 4, is added with stirring.

After 1 hour's heating, the mixture is diluted with 500 ml ice-cold water.

After neutralization with acetic acid, the expected product crystallizes.

It is recrystallized from methanol. It melts at 172° C.

Analysis of the product obtained gives the following results:

| Analysis | Calculated for $C_{13}H_{20}N_2O_6$ | Found |
|---|---|---|
| C % | 51.99 | 52.09 |
| H % | 6.71 | 6.76 |
| N % | 9.33 | 9.32 |
| O % | 31.97 | 31.90 |

EXAMPLE 13

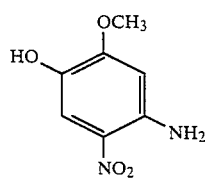

Preparation of 2-methoxy-4-amino-5-nitrophenol

A mixture consisting of 0.03 mol (5.5 g) of 2-amino-4,5-methylenedioxy-1-nitrobenzene and 22 g of sodium methylate in 30% strength solution in ethanol, to which 15 ml of methanol have been added, is heated to 55°–60° C. for 30 minutes.

After the reaction medium has been cooled in an ice bath, the sodium phenate of the expected product is drained. The phenate is dissolved in 60 ml of water. After neutralization with acetic acid, the expected product precipitates. After being washed with water and dried under vacuum in the presence of phosphorus pentoxide, it is recrystallized from ethyl acetate. A hot filtration enables a brown insoluble material to be removed. It melts at 171° C. Analysis of the product obtained gives the following results:

| Analysis | Calculated for $C_7H_8N_2O_4$ | Found |
|---|---|---|
| C % | 45.65 | 45.56 |
| H % | 4.38 | 4.42 |
| N % | 15.21 | 15.18 |
| O % | 34.75 | 34.64 |

EXAMPLE 14

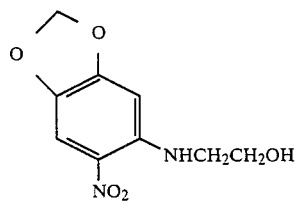

Preparation of 2-(β-hydroxyethyl)amino-4,5-methylenedioxy-1-nitrobenzene

A solution of 0.4 mol (24.0 g) of ethanolamine in 20 ml of 96° strength ethanol is added dropwise to a solution of 0.2 mol (42.4 g) of 4,5-methylenedioxy-1,2-dinotrobenzene in 60 ml of 96° strength ethanol and 30.7 ml of triethylamine brought to reflux. The heating is maintained for ½ hour after the addition is complete.

The reaction medium is poured onto 400 g of ice. After acidification with hydrochloric acid, the expected product precipitates. After being drained and made into a paste in water, it is recrystallized from 96° strength alcohol. It melts at 152° C.

| Analysis | Calculated for $C_9H_{10}N_2O_5$ | Found |
|---|---|---|
| C % | 47.79 | 47.58 |
| H % | 4.46 | 4.44 |
| N % | 12.39 | 12.34 |
| O % | 35.37 | 35.34 |

EXAMPLE 15

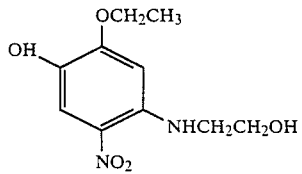

Preparation of 2-ethoxy-4-(β-hydroxyethyl)amino-5-nitrophenol 0.16 mol (10.5 g) of 85% pure potassium hydroxide pellets are dissolved in 80 ml of absolute ethanol on a boiling water bath. 0.08 mol (18.1 g) of 2-(β-hydroxyethyl)amino-4,5-methylenedioxy-1-nitrobenzene is added with stirring in the course of 10 minutes.

After 45 minutes' heating, the reaction medium is poured into 200 g of ice-cold water; the expected product precipitates after neutralization of the medium with acetic acid. It is recrystallized from 96° strength ethanol. It melts at 203° C.

Analysis of the product obtained gives the following results:

| Analysis | Calculated for $C_{10}H_{14}N_2O_5$ | Found |
|---|---|---|
| C % | 49.58 | 49.32 |
| H % | 5.83 | 5.86 |
| N % | 11.57 | 11.66 |
| O % | 33.03 | 32.86 |

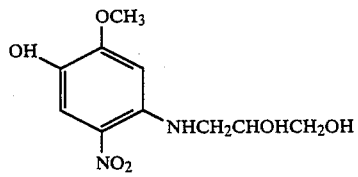

Preparation of 2-methoxy-4-($\beta,\gamma$-dihydroxypropyl)amino-5-nitrophenol

A mixture consisting of 0.06 mol (15.6 g) of 2-($\beta,\gamma$-dihydroxypropyl)amino-4,5-methylenedioxy-1-nitrobenzene, prepared according to Example 6, and 50 ml of a 5N solution of sodium methylate in methanol, to which solution 25 ml of methanol have been added, is heated to the refluxing temperature of the methanol for 20 minutes.

After the reaction medium has been cooled in an ice bath, the sodium phenate of the expected product is drained. The phenate is suspended in 70 ml of water. After neutralization with acetic acid, the expected product precipitates. After being washed with water and dried under vacuum in the presence of phosphorus pentoxide, it is recrystallized from dioxane. A hot filtration enables a brown insoluble material to be removed. It melts at 180° C.

Analysis of the product obtained gives the following results:

| Analysis | Calculated for $C_{10}H_{14}N_2O_6$ | Found |
|---|---|---|
| C % | 46.51 | 46.68 |
| H % | 5.47 | 5.47 |
| N % | 10.85 | 10.81 |
| O % | 37.18 | 37.20 |

DYEING EXAMPLE 1

The following dyeing composition is prepared:

| | |
|---|---|
| 2-Amino-4,5-methylenedioxy-1-nitrobenzene | 0.38 g |
| 96° strength alcohol | 10 g |
| LAURAMIDE | 1.5 g |
| Lauric acid | 1 g |
| CELLOSIZE W.P. 03 | 5 g |
| Monoethanolamine | 2 g |
| Water qs | 100 g |
| pH 9.5 | |

When applied for 35 minutes at 28° C. on bleached hair, this mixture endows it, after shampooing and rinsing, with a powerful green-yellow colouring.

DYEING EXAMPLE 2

The following dyeing composition is prepared:

| | |
|---|---|
| 2-Methylamino-4,5-methylenedioxy-1-nitrobenzene | 0.21 g |
| Propylene glycol | 10 g |
| 96° alcohol | 10 g |
| CELLOSIZE W.P. 03 | 2 g |
| Cetyldimethylhydroxyethylammonium chloride | 2 g |
| Triethanolamine in aqueous solution, 1% by weight | 0.4 g |
| Water qs | 100 g |
| pH 7.5 | |

When applied for 20 minutes at 28° C. on bleached hair, this mixture endows it, after shampooing and rinsing, with a golden beige colouring.

DYEING EXAMPLE 3

The following dyeing composition is prepared:

| | |
|---|---|
| 2-Butylamino-4,5-methylenedioxy-1-nitrobenzene | 0.53 g |
| 2-Butoxyethanol | 10 g |
| CEMULSOL NP 4 | 12 g |
| CEMULSOL NP 9 | 15 g |
| Glycerolated oleyl alcohol containing 2 mols of glycerol | 1.5 g |
| Glycerolated oleyl alcohol containing 4 mols of glycerol | 1.5 g |
| Triethanolamine in aqueous solution, 1% by weight | 0.3 g |
| Water qs | 100 g |
| pH 7.2 | |

When applied for 20 minutes at 30° C. on bleached hair, this mixture endows it, after shampooing and rinsing, with a very pale straw colouring.

DYEING EXAMPLE 4

The following dyeing composition is prepared:

| | |
|---|---|
| 2-($\gamma$-Hydroxyproyl)amino-4,5-methylenedioxy-1-nitrobenzene | 0.12 g |
| 2-Butoxyethanol | 10 g |
| 96° strength alcohol | 10 g |
| CEMULSOL NP 4 | 12 g |
| CEMULSOL NP 9 | 15 g |
| Glycerolated oleyl alcohol containing 2 mols of glycerol | 1.5 g |
| Glycerolated oleyl alcohol containing 4 mols of glycerol | 1.5 g |
| 2-Amino-2-methyl-1-propanol in aqueous solution, 25 % by weight | 0.5 g |
| Water qs | 100 g |
| pH 10.3 | |

When applied for 25 minutes at 30° C. on bleached hair, this mixture endows it, after shampooing and rinsing, with a golden beige colouring.

DYEING EXAMPLE 5

The following dyeing composition is prepared:

| | |
|---|---|
| 2-($\beta$-Methoxyethyl)amino-4,5-methylenedioxy-1-nitrobenzene | 0.06 g |
| 96° strength alcohol | 10 g |
| COMPERLAN KD | 2.2 g |
| Lauric acid | 0.8 g |
| Ethylene glycol monoethyl ether | 2 g |
| Monoethanolamine | 1 g |
| Water qs | 100 g |
| pH 8.2 | |

When applied for 30 minutes at 28° C. on hair which is naturally 90% white, this mixture endows it, after shampooing and rinsing, with a pale golden yellow colouring.

DYEING EXAMPLE 6

The following dyeing composition is prepared:

| | |
|---|---|
| 2-(β,γ-Dihydroxypropyl)amino-4,5-methylenedioxy-1-nitrobenzene | 0.6 g |
| 2-Butoxyethanol | 10 g |
| ALFOL C 16/18 | 8 g |
| LANETTE wax E | 0.5 g |
| CEMULSOL B | 1 g |
| Oleic diethanolamide | 1.5 g |
| Triethanolamine solution, 1% by weight | 0.3 g |
| Water qs | 100 g |
| pH 7.4 | |

When applied for 35 minutes at 30° C. on hair which is naturally 90% white, this mixture endows it, after shampooing and rinsing with a powerful golden orange colouring.

DYEING EXAMPLE 7

The following dyeing composition is prepared:

| | |
|---|---|
| 2-Methoxy-4-methylamino-5-nitrophenol | 0.2 g |
| Propylene glycol | 10 g |
| 96° strength alcohol | 10 g |
| CEMULSOL NP 4 | 12 g |
| CEMULSOL NP 9 | 15 g |
| Glycolerated oleyl alcohol containing 2 mols of glycerol | 1.5 g |
| Glycolerated oleyl alcohol containing 4 mols of glycerol | 1.5 g |
| 2-amino-2-methyl-1-propanol in 25% aqueous solution | 0.5 g |
| Water qs | 100 g |
| pH 9.8 | |

When applied for 15 minutes at 28° C. on bleached hair, this mixture endows it, after shampooing and rinsing, with a pearly pale orange colouring.

DYEING EXAMPLE 8

The following dyeing composition is prepared:

| | |
|---|---|
| 2-(β-Hydroxyethoxy)-4-methylamino-5-nitrophenol | 0.5 g |
| 96° strength alcohol | 10 g |
| LAURAMIDE | 1.5 g |
| Lauric acid | 1 g |
| CELLOSIZE W.P. 03 | 5 g |
| Monoethanolamine | 2 g |
| Water qs | 100 g |
| pH 9.5 | |

When applied for 25 minutes at 28° C. on hair which is naturally 90% white, this mixture endows it, after shampooing and rinsing, with a pale red-orange colouring.

DYEING EXAMPLE 9

The following dyeing composition is prepared:

| | |
|---|---|
| 2-Methoxy-4-(γ-hydroxypropyl)amino-5-nitrophenol | 0.07 g |
| 2-Butoxyethanol | 20 g |
| CELLOSIZE W.P. 03 | 2 g |
| Ammonium lauryl sulphate | 5 g |
| Triethanolamine in 1% solution in water | 1 g |
| Water qs | 100 g |
| pH 8.1 | |

When applied for 30 minutes at 28° C. on bleached hair, this mixture endows it, after shampooing and rinsing, with a pale salmon-pink colouring.

DYEING EXAMPLE 10

The following dyeing composition is prepared:

| | |
|---|---|
| 2-(β,γ-Dihydroxypropoxy-4-n-butylamino-5-nitrophenol | 0.72 g |
| 2-Butoxyethanol | 10 g |
| ALFOL C 16/18 | 8 g |
| LANETTE wax E | 0.5 g |
| CEMULSOL B | 1 g |
| Oleic diethanolamide | 1.5 g |
| Monoethanolamine in 20% solution in water | 0.2 g |
| Water qs | 100 g |
| pH 8.5 | |

When applied for 20 minutes at 30° C. on bleached hair, this mixture endows it, after shampooing and rinsing, with a pale salmon-pink colouring.

DYEING EXAMPLE 11

The following dyeing composition is prepared:

| | |
|---|---|
| 2-Methoxy-4-n-butylamino-5-nitrophenol | 0.1 g |
| 2-Butoxyethanol | 10 g |
| COMPERLAN KD | 2.2 g |
| Lauric acid | 0.8 g |
| Ethylene glycol monoethyl ether | 2 g |
| Monoethanolamine | 1 g |
| Water qs | 100 g |
| pH 7.2 | |

When applied for 30 minutes at 30° C. on hair which is naturally 90% white, this mixture endows it, after shampooing and rinsing, with an orange-beige colouring.

DYEING EXAMPLE 12

The following dyeing composition is prepared:

| | |
|---|---|
| 2-Methoxy-4-amino-5-nitrophenol | 0.1 g |
| 2-Butoxyethanol | 10 g |
| CELLOSIZE WP 03 | 2 g |
| Cetyldimethylhydroxyethylammonium chloride | 2 g |
| Ammonia, 5% in water | 0.9 g |
| Water qs | 100 g |
| pH 9 | |

When applied for 30 minutes at 30° C. on bleached hair, this mixture endows it, after shampooing and rinsing, with an intense orange-yellow colouring.

DYEING EXAMPLE 13

The following dyeing composition is prepared:

| | |
|---|---|
| 2-Ethoxy-4-(β-hydroxyethyl)amino-5-nitrophenol | 1.5 g |
| ALFOL C 16/18 | 8 g |
| LANETTE wax E | 0.5 g |
| CEMULSOL B | 1 g |
| Oleic diethanolamide | 1.5 g |
| 20% strength NH₄OH | 10 g |
| 2-Butoxyethanol | 10 g |
| Water qs | 100 g |

-continued

| | |
|---|---|
| pH 10.5 | |

When applied for 30 minutes at 30° C. on hair which is naturally 90% white, this mixture endows it, after shampooing and rinsing, with an intense orange-yellow colouring.

DYEING EXAMPLE 14

The following dyeing composition is prepared:

| | |
|---|---|
| 2-Methoxy-4-(β,γ-dihydroxypropyl)amino-5-nitrophenol | 2 g |
| 2-Butoxyethanol | 10 g |
| CELLOSIZE W.P. 03 | 2 g |
| Cetyldimethylhydroxyethylammonium chloride | 2 g |
| Triethanolamine qs pH 9.5 | |
| Water qs | 100 g |

When applied for 30 minutes at 28° C. on hair which is naturally 90% white, this mixture endows it, after shampooing and rinsing, with a dazzling orange colouring.

The different trade names used in the above examples are clarified in greater detail below:

CEMULSOL NP₄ : oxyethylenated nonylphenol containing 4 mols of ethyleneoxide, sold by RHONE POULENC.

CEMULSOL NP₉ : oxyethylenated nonylphenol containing 9 mols of ethyleneoxide, sold by RHONE POULENC.

ALFOL C₁₆/₁₈ (50/50) : cetyl-stearyl alcohol, sold by CONDEA.

LANNETTE wax E : Sodium cetyl-stearyl sulphate, sold by HENKEL.

CEMULSOL B : ethoxylated castor oil, sold by RHONE POULENC.

LAURAMIDE : lauric acid monoethanolamide, sold by WITCO.

CELLOSIZE WP 03 : hydroxyethylcellulose, sold by UNION CARBIDE.

COMPERLAN KD : coconut fatty acid diethanolamide, sold by HENKEL.

We claim:

1. A composition for dyeing human hair comprising, in a cosmetically acceptable medium and in an amount ranging from 0.001 to 5 weight percent based on the total weight of said composition, at least one compound of formula II'

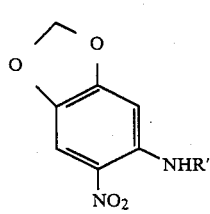

(II')

wherein R' represents hydroxyalkyl having 1-6 carbon atoms, polyhydroxyalkyl having 2-6 carbon atoms or alkoxyalkyl wherein the alkoxy moiety has 1-3 carbon atoms and the alkyl moiety has 1-6 carbon atoms, said composition having a pH between 3 and 11.5.

2. A process for direct dyeing human hair comprising applying to said hair in an amount sufficient to dye said hair a composition comprising, in a cosmetically acceptable medium and in an amount ranging from 0.001 to 5 weight percent based on the total weight of said composition, at least one compound of formula II

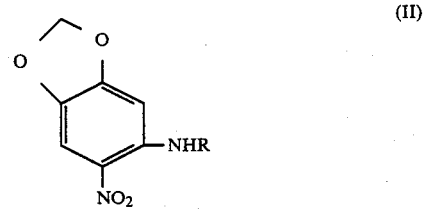

(II)

wherein R represents hydrogen, alkyl having 1-6 carbon atoms, hydroxyalkyl having 1-6 carbon atoms, polyhydroxyalkyl having 2-6 carbon atoms or alkoxy alkyl wherein the alkoxy moiety has 1-3 carbon atoms and the alkyl moiety has 1-6 carbon atoms, permitting said composition to remain in contact with said hair for a period of time ranging from 5 to 40 minutes, rinsing said hair and drying said hair.

3. The process of claim 2 wherein, subsequent to rinsing said hair, the rinsed hair is shampooed and rinsed again before drying said hair.

4. The composition of claim 1 which also includes a hair dyeing amount of a compound of the formula I

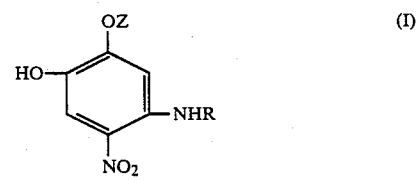

(I)

wherein

Z represents —CH₂W wherein W represents hydrogen, alkyl having 1-6 carbon atoms, hydroxyalkyl having 1-6 carbon atoms, polyhydroxyalkyl having 2-6 carbon atoms, alkoxyalkyl wherein the alkoxy moiety has 1-3 carbon atoms and the alkyl moiety has 1-6 carbon atoms or hydroxyalkoxyalkyl wherein the alkoxy moiety has 1-3 carbon atoms and the alkyl moiety has 1-6 carbon atoms, and R represents hydrogen, alkyl having 1-6 carbon atoms, hydroxyalkyl having 1-6 carbon atoms, polyhydroxyalkyl having 2-6 carbon atoms or alkoxyalkyl wherein the alkoxy moiety has 1-3 carbon atoms and the alkyl moiety has 1-6 carbon atoms.

5. The composition of claim 4 wherein Z represents methyl, ethyl, n-propyl, β-hydroxyethyl, β,γ-dihydroxypropyl, γ-hydroxypropyl, β-methoxyethyl, β-ethoxyethyl or β-hydroxyethoxyethyl and R represents methyl, ethyl, n-propyl, n-butyl, β-hydroxyethyl, γ-hydroxypropyl, β,γ-dihydroxypropyl, β-methoxyethyl or β-ethoxyethyl.

6. The dye composition of claim 4 wherein the compound of formula I is selected from the group consisting of 2-methoxy-4-methylamino-5-nitrophenol,
2-methoxy-4-n-butylamino-5-nitrophenol,
2-methoxy-4-(γ-hydroxypropyl)-amino-5-nitrophenol,
2-(β-hydroxyethoxy)-4-methylamino-5-nitrophenol,
2-(β,γ-dihydroxypropoxy)-4-n-butylamino-5-nitrophenol, 2-methoxy-4-amino-5-nitrophenol,
2-ethoxy-4-(β-hydroxyethyl)amino-5-nitrophenol and
2-methoxy-4-(β,γ-dihydroxypropyl)amino-5-nitrophenol.

7. The composition of claim 1 wherein said compound of formula II' is present in an amount ranging from 0.01 to 3 weight percent.

8. The composition of claim 4 wherein said compound of formula I is present in an amount ranging from 0.001 to 5 weight percent based on the total weight of said composition.

9. The composition of claim 8 wherein said compound of formula I is present in an amount ranging from 0.01 to 3 weight percent.

10. The composition of claim 1 wherein said cosmetically acceptable medium is water or a mixture of water and a solvent, said solvent being a lower alkanol, a polyol, a glycol, a glycol ether or a mixture thereof, said solvent being present in an amount ranging from 1 to 75 percent by weight based on the total weight of said composition.

11. The composition of claim 10 wherein said solvent is present in an amount ranging from 5 to 50 percent by weight based on the total weight of said composition.

12. The composition of claim 1 which also contains an anionic, cationic, nonionic or amphoteric surfactant, or a mixture thereof, said surfactant being present in an amount ranging from 0.5 to 55 percent by weight based on the total weight of said composition.

13. The composition of claim 12 wherein said surfactant is present in an amount ranging from 4 to 40 percent by weight based on the total weight of said composition.

14. The composition of claim 1 which also contains a thickener in an amount ranging from 0.1 to 3 percent by weight based on the total weight of said composition.

15. The composition of claim 14 wherein said thickener is present in an amount ranging from 0.5 to 3 percent by weight based on the total weight of said composition.

16. The composition of claim 1 which also contains at least one of a penetrant, a sequestering agent, a film forming agent, a buffer and a perfume.

17. The composition of claim 1 having a pH between 5 and 11.5.

18. The composition of claim 1 which also contains in addition to the said compound of formula II' another direct hair dye selected from the group consisting of an azo dye, an anthraquinone dye and a nitrobenzene dye other than dye of formula II', said another direct dye being present in an amount ranging from 0.001 to 5 percent by weight based on the total weight of said composition.

19. The composition of claim 1, in the form of a hair setting lotion, wherein said cosmetically acceptable medium is an alcoholic or hydroalcoholic solution and said composition also contains at least one cosmetic resin in an amount sufficient to set the hair.

20. A composition for dyeing human hair comprising in a cosmetically acceptable medium a hair dyeing amount of
(i) at least one compound of formula I

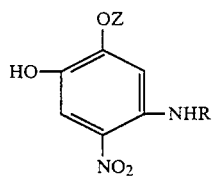

wherein
Z represents —CH$_2$W wherein W represents hydrogen, alkyl having 1-6 carbon atoms, hydroxyalkyl having 1-6 carbon atoms, polyhydroxyalkyl having 2-6 carbon atoms, alkoxyalkyl wherein the alkoxy moiety has 1-3 carbon atoms and the alkly moiety has 1-6 carbon atoms or hydroxyalkoxyalkyl wherein the alkoxy moiety has 1-3 carbon atoms and the alkyl moiety has 1-6 carbon atoms, and
R represents hydrogen, alkyl having 1-6 carbon atoms, hydroxyalkyl having 1-6 carbon atoms, polyhydroxyalkyl having 2-6 carbon atoms or alkoxyalkyl wherein the alkoxy moiety has 1-3 carbon atoms and the alkyl moiety has 1-6 carbon atoms, and
(ii) at least one compound of formula (II')

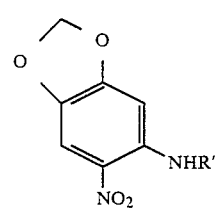

wherein R' represents hydroxyalkyl having 1-6 carbon atoms, polyhydroxyalkyl having 2-6 carbon atoms or alkoxyalkyl wherein the alkoxy moiety has 1-3 carbon atoms and the alkyl moiety has 1-6 carbon atoms.

21. The composition of claim 2 wherein said compound of formula I, Z represents methyl, ethyl, n-propyl, β-hydroxyethyl, β, γ-dihydroxypropyl, γ-hydroxypropyl, β-methoxyethyl, β-ethoxyethyl or β-hydroxyethoxyethyl and R represents hydrogen, methyl, ethyl, n-propyl, n-butyl, β-hydroxyethyl, γ-hydroxypropyl, β, γ-dihydroxypropyl, β-methoxyethyl or β-ethoxyethyl.

22. The dye composition of claim 20 wherein the compound of formula I is selected from the group consisting of
2-methoxy-4-methylamino-5-nitrophenol,
2-methoxy-4-n-butylamino-5-nitrophenol,
2-methoxy-4-(γ-hydroxypropyl)-amino-5-nitrophenol,
2-(β-hydroxyethoxy)-4-methylamino-5-nitrophenol,
2-(β, γ-dihydroxypropoxy)-4-n-butylamino-5-nitrophenol,
2-methoxy-4-amino-5-nitrophenol,
2-ethoxy-4-(β-hydroxyethyl) amino-5-nitrophenol and
2-methoxy-4-(β, γ-dihydroxypropyl) amino-5-nitrophenol.

23. The dye composition of claim 20 wherein the compound of formula II' is selected from the group consisting of
2-(γ-hydroxypropyl) amino-4,5-methylenedioxy-1-nitrobenzene, 2-(β-hydroxyethyl) amino-4,5-methylenedioxy-1-nitrobenzene, 2-(β, γ-dihydroxypropyl) amino-4,5-methylenedioxy-1-nitrobenzene and 2-(β-methoxyethyl) amino-4,5-methylenedioxy-1-nitrobenzene.

24. The composition of claim 20 wherein said cosmetically acceptable medium is water or a mixture of water and a solvent, said solvent being a lower alkanol, a polyol, a glycol, a glycol ether or a mixture thereof, said solvent being present in an amount ranging from 1 to 75 percent by weight based on the total weight of said composition.

25. The composition of claim 24 wherein said solvent is present in an amount ranging from 5 to 50 percent by weight based on the total weight of said composition.

26. The composition of claim 20 which also contains an anionic, cationic, nonionic or amphoteric surfactant, or a mixture thereof, said surfactant being present in an amount ranging from 0.5 to 55 percent by weight based on the total weight of said composition.

27. The composition of claim 26 wherein said surfactant is present in an amount ranging from 4 to 40 percent by weight based on the total weight of said composition.

28. The composition of claim 20 which also contains a thickener in an amount ranging from 0.1 to 3 percent by weight based on the total weight of said composition.

29. The composition of claim 28 wherein said thickener is present in an amount ranging from 0.5 to 3 percent by weight based on the total weight of said composition.

30. The composition of claim 20 which also contains at least one of a penetrant, a sequestering agent, a film forming agent, a buffer and a perfume.

31. The composition of claim 20 having a pH between 3 and 11.5.

32. The composition of claim 20 having a pH between 5 and 11.5.

33. The composition of claim 20 which also contains in addition to the said nitroaminophenol, another direct hair dye selected from the group consisting of an azo dye, an anthraquinone dye and a nitrobenzene dye other than the dye of formula II', said another direct dye being present in an amount ranging from 0.001 to 5 percent by weight based on the total weight of said composition.

34. The composition of claim 20, in the form of a hair setting lotion, wherein said cosmetically acceptable medium is an alcoholic or hydroalcoholic solution and said hair the composition of claim 20, permitting said resin in an amount sufficient to set the hair.

35. A process for direct dyeing human hair comprising applying to said hair in an amount sufficient to dye said hair the composition of claim 40, permitting said composition to remain in contact with said hair for a period of time ranging from 5 to 40 minutes, rinsing said hair and drying said hair.

36. The process of claim 35 wherein, subsequent to rinsing said hair, the rinsed hair is shampooed and rinsed again before drying said hair.

* * * * *